(12) United States Patent
Weaver et al.

(10) Patent No.: US 7,182,817 B1
(45) Date of Patent: Feb. 27, 2007

(54) APPARATUS AND METHOD FOR DEVELOPING LATENT FINGERPRINTS

(76) Inventors: David E. Weaver, P.O. Box 179, Lookout, WV (US) 25868; Ordis G. Weaver, 6107 W. Bogart Rd., Castalia, OH (US) 44824

( * ) Notice: Subject to any disclaimer, the term of this patent is extended or adjusted under 35 U.S.C. 154(b) by 0 days.

(21) Appl. No.: 11/406,096

(22) Filed: Apr. 18, 2006

(51) Int. Cl.
C23C 16/448 (2006.01)
C23C 16/00 (2006.01)

(52) U.S. Cl. ..................... 118/715; 118/31.5
(58) Field of Classification Search ............... 118/715, 118/31.5
See application file for complete search history.

(56) References Cited

U.S. PATENT DOCUMENTS

| | | | |
|---|---|---|---|
| 4,550,041 A * | 10/1985 | Thompson et al. | 206/524.3 |
| 4,556,579 A | 12/1985 | Lowell | |
| 4,613,515 A | 9/1986 | Reggio | |
| 5,281,293 A | 1/1994 | Frame et al. | |
| 5,342,645 A | 8/1994 | Eisele et al. | |
| 5,348,759 A | 9/1994 | Weaver et al. | |
| 5,395,445 A | 3/1995 | Bohanan | |
| 5,424,092 A | 6/1995 | Weaver et al. | |
| 5,906,871 A | 5/1999 | Takebe et al. | |
| 6,423,946 B1 | 7/2002 | Berka et al. | |

* cited by examiner

Primary Examiner—Jeffrie R. Lund
(74) Attorney, Agent, or Firm—Thompson Hine LLP

(57) ABSTRACT

An apparatus and method for developing latent fingerprints has a breakable capsule containing a cyanoacrylate monomer disposed within an internal chamber of a housing containing a cyanoacrylate catalyst and being adapted for emitting vapors. The housing is impregnated with the cyanoacrylate catalyst or has a layer of cyanoacrylate catalyst on a portion of its interior surface. The apparatus optionally has a breakable capsule breaking mechanism for assisting a user in breaking the breakable capsule within the housing. Upon breaking the breakable capsule, the cyanoacrylate monomer spilling from the breakable capsule reacts with the cyanoacrylate catalyst contained in the housing to create vapor fumes. The vapor fumes contact an object being tested to reveal any latent fingerprints on the object. The apparatus is sized such that it is adapted for placing in any container, room, vehicle, or appropriate open space.

16 Claims, 3 Drawing Sheets

APPARATUS AND METHOD FOR DEVELOPING LATENT FINGERPRINTS

BACKGROUND

1. Technical Field

The present invention relates to apparatuses for developing latent fingerprints and the method of use thereof, and in particular, to a portable and disposable apparatus containing a cyanoacrylate catalyst and a cyanoacrylate monomer which upon combination thereof creates a cyanoacrylate vapor used in the quick and efficient development of latent fingerprints.

2. Related Art

The use of cyanoacrylate monomers and catalysts in the development of latent fingerprints on objects is well known and has been used as such for many years. Specifically, it is the reaction of the cyanoacrylate monomer and catalyst that creates a microcrystalline vapor which adheres to fingerprints. Once the vapor cures, the cyanoacrylate forms a white polymer substance that reveals the fingerprint.

U.S. Pat. No. 4,556,579 to Lowell discloses a kit for developing latent fingerprints wherein liquid cyanoacrylate monomer is deposited onto a porous fiber plug made of cellulose acetate fibers. The resulting fumes from the chemical reaction generate any latent fingerprints that come into contact with the fumes. The kit also has a solvent for removing such fingerprints when desired.

Similar to the '579 patent, U.S. Pat. No. 4,613,515 to Reggio also discloses a kit for developing latent fingerprints on a solid surface. The kit contains an absorbent pad impregnated with a cyanoacrylic polymerization catalyst and one or more initiators, a promoter and an accelerator. The kit also provides a separate source of a polymerizable alpha-cyanoacrylate monomer with at least one inhibitor agent. In operation, a cyanoacrylate monomer is added to the surface of the pad and the pad is placed adjacent a surface believed to contain a fingerprint. The pad remains undisturbed until it generates a microcrystalline vapor from the reaction of the cyanoacrylic catalyst and monomer. The vapor travels through the air to the solid surface wherein upon contact with the surface it adheres to the latent fingerprint, thereby making the latent fingerprint visible.

There are several disadvantages with the kits of the '579 and '515 patents. The user must physically add the cyanoacrylate monomer to a pad or plug which may result in unwanted spillage or a wrong amount of cyanoacrylate monomer applied to the pad. The kits also consist of multiple components which increases the complexity of using the kits as well as increases the amount of waste.

U.S. Pat. No. 5,342,645 to Eisele, et al. discloses a metal cartridge containing a porous or fibrous pad such as steel or glass wool, impregnated with a cyanoacrylate ester and a volatile, emissive lanthanide metal-complex or actinide metal-complex. Upon the application of heat, e.g., a butane-powered torch, the chemical reaction produces a chemical vapor that is used to develop latent fingerprints. The principal disadvantages with the '645 patent is that it requires a heat resistant housing and the use of a butane torch, both requirements making the cartridge clumsy and potentially dangerous to use.

U.S. Pat. Nos. 5,348,759 and 5,424,092 to Weaver, et al. disclose a device for developing latent fingerprints. The device has a housing that contains a cyanoacrylate (either in liquid or solid form) and is adapted to receive a propane torch. Upon lighting the torch, the cyanoacrylate is vaporized and propelled toward the object to be tested on which any latent fingerprints appear within minutes. The user may replace the cyanoacrylate as needed for new tests. The disadvantage with these devices is that they require the use of a propane torch which increases the potential danger of using the devices. The devices also have multiple components including the need for additional cyanoacrylate to refill the housing, which increases the maintenance of the devices.

U.S. Pat. No. 5,395,445 to Bohanan discloses a method and apparatus for developing latent fingerprints on a portion of skin. The apparatus uses a heater to create a cyanoacrylate vapor which is propelled by a fan through a hose and comes in contact with skin. As seen in previous devices, this apparatus is very cumbersome to carry and use in field operation, and requires the use of a separate heater and fan which increases the maintenance effort.

U.S. Pat. No. 6,423,946 to Berka, et al. discloses an apparatus for developing latent fingerprints having a sealable container for depositing objects being tested for fingerprints. The container has an electrical heater as well as an exhaust means for evacuating air from the internal chamber. In operation, the method includes heating the container, placing objects within the chamber, adding a few drops of cyanoacrylate on an upper surface of an internal receptacle, covering the container, and pumping air from the container. After the fumes have developed any latent fingerprints on the objects within the chamber, the cover is removed and the objects are taken out. The disadvantage with the '946 device is that it is cumbersome to carry and use in the field. The user requires an electrical outlet for powering the heater. Also, the internal size of the chamber limits the number, size, and shape of the objects that can be placed in the container for testing.

Therefore, upon review of the prior art, there is a need for a simple, self-contained, disposable apparatus for developing latent fingerprints which eliminates the guesswork in the measuring and mixing of cyanoacrylate monomer to apply to a cyanoacrylate catalyst, eliminates the need to locate and maintain multiple components, eliminates the need for a heater source, and is easily adaptable to use in any location and with any size object being tested.

SUMMARY OF THE INVENTION

The present invention solves the problems of the prior art with an apparatus having a breakable capsule containing a cyanoacrylate monomer disposed within a housing containing a cyanoacrylate catalyst and being adapted for emitting vapors. The housing is impregnated with the cyanoacrylate catalyst or has a layer of cyanoacrylate catalyst on a portion of its interior surface. Upon breaking the capsule, the cyanoacrylate monomer spilling from the capsule reacts with the cyanoacrylate catalyst contained in the housing to create vapor fumes. The fumes are emitted from the housing through pores, perforations, slits, mesh, or open spaces or sides of the housing. The vapor fumes contact an object being tested and reveal any latent fingerprints on the object. The apparatus is sized such that it is adapted for placing in any container, room, vehicle, or appropriate open space. The apparatus is intended to be a disposable product available in single and multiple packets that are stored within a wrapper prior to use.

The apparatus optionally has a capsule breaking mechanism for assisting a user in breaking the capsule within the housing. The capsule breaking mechanism may be disposed within the housing or positioned external to the housing. Also, the breakable capsule may be secured within the capsule breaking mechanism prior to use.

Other features and objectives of the present invention are set forth more fully herein.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawings in which the reference number first appears.

DETAILED DESCRIPTION OF THE INVENTION

Figure 1:
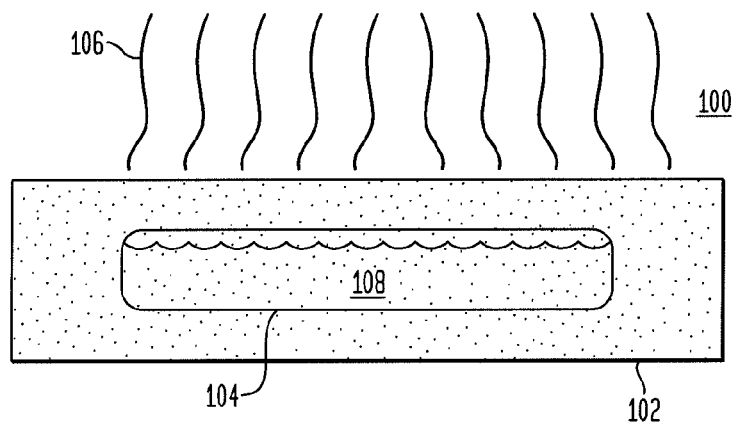
FIG. 1 is a planar side view of an apparatus of the present invention.

As shown in FIG. 1, the present invention is an apparatus 100 having a porous, e.g., a cellulosic fiber housing 102 impregnated with any cyanoacrylate catalyst. A breakable capsule 104 (or capsule 104) of liquid cyanoacrylate monomer 108 is contained within an internal chamber of the housing 102.

In the preferred and simplest embodiment, the housing 102 is a porous material. For example, the housing 102 is a cellulosic fiber material of paper, fibrous textile, plastic, metal, resin, composite, and the like. Alternatively, the housing 102 may be made of a perforated material, e.g., plastic, composite, paper, or resin coated paper, that has holes, perforation, slits, or mesh. Regardless of the particular material, the housing 102 must have a means for emitting vapors 106 as well as for containing a cyanoacrylate catalyst. The material of the housing 102 is preferably impregnated with cyanoacrylate catalyst. It is well known to one of ordinary skill in the relevant art to impregnate the housing 102 with a cyanoacrylate catalyst using such methods as spraying, dipping, soaking, wiping, and similar processes.

The breakable capsule 104 is made of a material such that it is adapted for breaking or cracking easily thereby allowing the liquid cyanoacrylate monomer 108, e.g., "super glue," to spill out and into the housing 102. The capsule 104 is preferably made from a thin glass, plastic, ceramic, or resin coated paper—all of which can contain the liquid cyanoacrylate monomer 108 while remaining substantially easy to break or tear. Such breakable capsules 104 are well known in the relevant art.

Figure 3:
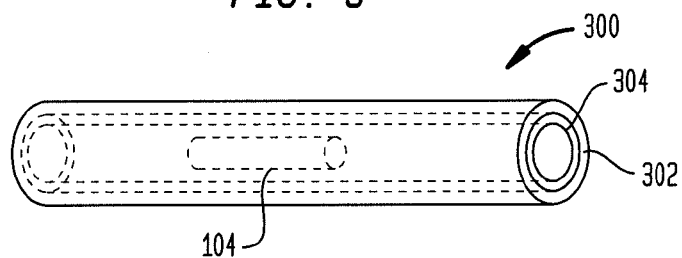
FIG. 3 is a perspective view of a second alternative embodiment of the apparatus.
Figure 4:
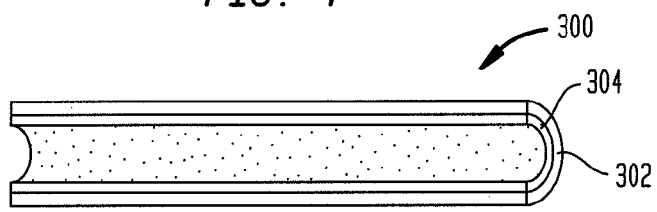
FIG. 4 is a cut-away perspective view of the second alternative embodiment.

Alternatively, as shown in FIGS. 3 and 4, an apparatus 300 is depicted having a housing 302 which is not impregnated with such a cyanoacrylate catalyst, but rather a layer 304 of a cyanoacrylate catalyst is applied to the housing 102, e.g., the interior surface of the housing 302. The layer 304 may cover either the entire interior surface of the housing 302 (as shown for convenience) or may cover a portion of the interior surface. For example, the cyanoacrylate catalyst may be applied to a central portion of the interior surface of the housing 302 only. In addition, the layer 304 of cyanoacrylate catalyst may be applied directly to the housing 102, i.e., the interior surface of the housing 102, by spraying, painting, dipping, wiping, etc. Also, the layer 304 may comprise a separate liner containing the cyanoacrylate catalyst that is then optionally secured to the interior surface via an adhesive, tape, hook and loop fastener (Velcro®), or a mechanical fastener such as a locking ring. If not secured to the housing 102, the liner slides into and fits within the internal chamber of the housing 102. If a liner is used, the liner may be impregnated with the cyanoacrylate catalyst or the cyanoacrylate catalyst may be contained on the inner surface of the liner. In either embodiment, the layer 304 (whether a direct application of a catalyst or a separate liner containing the catalyst) must be adapted to have a means for emitting vapors 106 through the layer 304 (including any liner used) and ultimately through the housing 302. Therefore, if the layer 304 is a separate liner, the liner must be a porous material (see FIG. 3) or have perforations (see FIG. 4), holes, slots, or a mesh for allowing the vapors 106 to pass through.

The housing 102, 302 is shown tubular in shape for convenience purpose only. When embodied in this shape, the preferred dimensions are about ½ of an inch in diameter and about 3 inches in length. The ends of the housing 102, 302 are preferably not capped or closed off, but rather, are open (see FIG. 3) to facilitate the emission of vapor 106. The shape and dimensions of the housing 102, 302 are described in these terms for convenience purpose only. It would be readily apparent to design a housing 102, 302 having a different shape and different dimensions while not interfering with performance. For example, the housing 102, 302 may be square, rectangular, circular, and the like, and may be scaled smaller or larger as required by the size of the objects and/or area from which latent fingerprints must be developed.

In addition, when the housing 102 has the preferred dimensions of about ½ of an inch in diameter by about 3 inches in length, the breakable capsule 104 is preferably oval in shape having preferred dimensions of about ⅜ inches in diameter (with a minimum diameter of about ¼ inches) and about ¾ inches in length. The entire breakable capsule 104 is filled or substantially filled with the liquid cyanoacrylate monomer 108. The breakable capsule 104 is described in terms of this shape and these dimensions for convenience purpose only. It would be readily apparent to use a comparable size and shape, and/or a different shape of breakable capsule 104 and achieve the same results; that is, the breakable capsule 104 is sized according to the size of the housing 102 (and amount of cyanoacrylate monomer 108) being used. Also, the housing 102 is impregnated with a pre-defined amount of a cyanoacrylate catalyst as to maximize the resulting vapor 106.

The exact dimensions of the breakable capsule 104, thus the maximum volume of liquid cyanoacrylate monomer 108 of the apparatus 100, and the amount of cyanoacrylate catalyst contained in the housing 102 are such that the maximum amount of vapor 106 is produced upon activation of the liquid cyanoacrylate monomer 108 and the cyanoacrylate catalyst. The use of these compounds, cyanoacrylate monomer 108 and cyanoacrylate catalyst, are very well known in the art of developing latent fingerprints. Thus, it is readily apparent to one of ordinary skill in the relevant arts to design, develop, and use an apparatus of specific compounds, dimensions and pre-defined amounts of the compounds, liquid cyanoacrylate monomer 108 and cyanoacrylate catalyst, to achieve the desired results of developing latent fingerprints as described herein.

In operation, referring to apparatus 100 for convenience purposes only, when the breakable capsule 104 is broken, the cyanoacrylate catalyst impregnated or contained in the housing 102 rapidly activates the cyanoacrylate monomer 108, thereby producing a microcrystalline vapor 106. The vapor 106 passes through the housing 102, and any object subjected or introduced to this vapor 106 will develop any existing latent fingerprints.

In addition, it is preferred that the apparatus 100 is used in conjunction with a container, box, aquarium, or any closed vessel. Thus, all objects that are to be examined for latent fingerprints, e.g., glasses, pens, keys, figurines, weapons, or any other object having in general a non-porous surface, are placed in, for example, a 10–15 gallon glass aquarium. An apparatus 100 is taken, the capsule 104 is broken within the housing 102 by simply cracking the capsule 104 by hand, and then the apparatus 100 is placed in the aquarium, and a cover is placed over the aquarium to seal it closed, thereby containing the vapor 106 in the aquarium. The cover does not have to provide a complete seal to the aquarium; however a tight seal is best wherein a tight seal provide minimal escape of the resulting vapor 106. After about 5–10 minutes, the cover may be removed and any latent fingerprints on the objects placed inside the aquarium are developed.

Further in operation, the apparatus 100 may be provided to the user as described herein; that is, with the breakable capsule 104 already contained within the housing 102. In this embodiment, the apparatus 100 may be stored prior to use in a cellophane wrapper, foil outer wrapper (similar to trade card wrappers), shrink-wrap, blister pack, or comparable wrapper such that the user must tear open the wrapper to access the apparatus 100. Alternatively, the user may receive the housing 102 separate from the breakable capsule 104 such that the user must insert the breakable capsule 104 into the housing 102 prior to use. In this embodiment, either the housing 102 or the breakable capsule 104 or both may be prepackaged in one or more wrappers. However, regardless of whether the user receives the apparatus 100 with the breakable capsule 104 pre-inserted into the housing 102 or the user inserts the capsule 104 into the housing 102 prior to use, it is preferred that the user breaks the capsule 104 when the capsule 104 is contained within the housing 102 or when the breakable capsule 104 is inserted into the housing 102.

Figure 2:
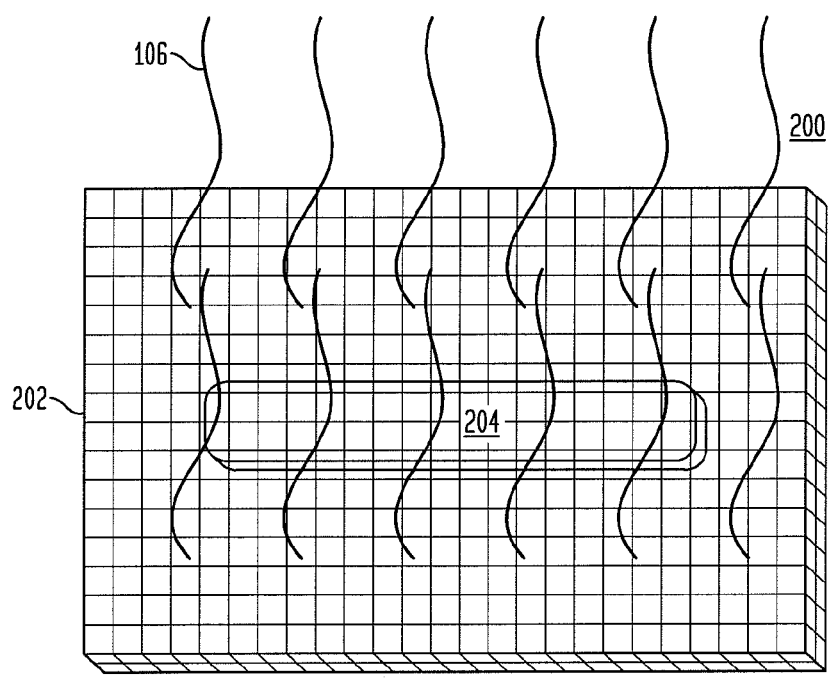
FIG. 2 is a perspective view of an alternative embodiment of the apparatus.

Another alternative embodiment of an apparatus 200 is shown in FIG. 2. In this embodiment, the apparatus 200 has a housing 202 that is a porous bag impregnated with any cyanoacrylate catalyst (as described above with apparatus 100). The housing 202 is preferably square in shape, being about 9 inches by 9 inches, but this is for convenience purposes only. The housing 202 may be any shape and size to accommodate larger areas being examined for latent fingerprints. The housing 202 is made of a screen type of material, such as a loose cellulosic fiber material, in order to allow the vapor 106 to pass inherently through the housing 202.

The apparatus 200 may optionally be sealed on all sides, or may have a resealable side such that one side opens to provide access to the internal cavity and then closes/reseals. See FIG. 5. Possible resealable sides include the use of hook and loop fasteners (Velcro®), snaps, pressure lock seals, a fold wherein a first side of the housing extends beyond the opposing second side such that the first side folds over the second side, etc. This allows a user to place a breakable capsule 204 of liquid cyanoacrylate monomer 108 inside the housing 202 along with an optional second capsule 504 as described below. The use of a resealable side also provides the means for reusing the housing 202 for multiple uses wherein each use of the housing 202 uses a new breakable capsule 104. Further, regarding such reuse of the housing 102, a new separate layer 304, i.e., a new liner, is inserted into the internal chamber of the housing 102 for each subsequent use of the housing 102.

Referring to FIG. 2, this apparatus 200 is best suited for developing latent fingerprints in large target areas such as a room in a home or office, or in a vehicle. In this use, the entries and exists of the target area are sealed off as best as possible by either closing doors and windows, and/or using plastic sheet. The breakable capsule 204 is broken in the apparatus 200, and then the apparatus 200 is placed into the target area, sealing off the location at which the apparatus 200 was placed into the area. Again, after about 5–10 minutes, the target area may be re-opened and any latent fingerprints on the objects and contents of the area are developed.

Figure 5:
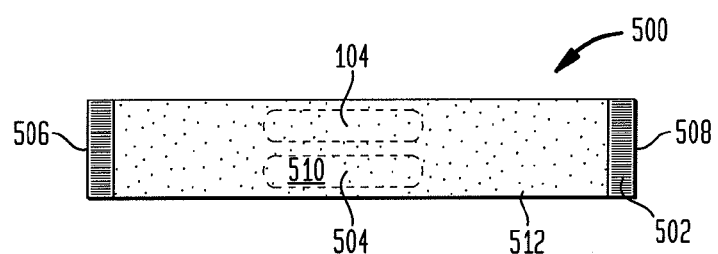
FIG. 5 is a perspective view of a third alternative embodiment of the apparatus.

An alternative apparatus 500 is shown in FIG. 5 which has a rectangular housing 512 wherein the two ends 506, 508 are sealed. The two ends 506, 508 may be permanently sealed, such that the apparatus 500 is a disposable product. For example, the end 508 is closed by a closing means 502 including an adhesive, heat sealing, stitches, or one or more mechanical fasteners. Thus, once the apparatus 500 is used, it is thrown away.

FIG. 5 also depicts the use of an optional second breakable capsule 504 containing a second catalyst or a sublimation dye 510. Thus, upon the breakage of the second breakable capsule 504, along with breaking the capsule 104, the sublimation dye 510 combines with the resulting vapor 106 thereby enhancing the development of latent fingerprints by adding color to the fingerprints. The use of sublimation dyes 510 in the development of latent fingerprints is well known in the relevant art.

Figure 6:
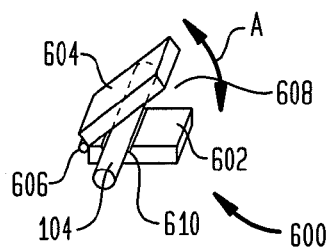
FIG. 6 is a perspective view of a capsule breaking mechanism.

FIG. 6 is a perspective view of a capsule breaking mechanism 600 which may optionally be used to assist in breaking a capsule 104 or 504 of the present invention. The capsule breaking mechanism 600 has a bottom half 602 and a top half 604 that are pivotally and movably connected together. In one embodiment, a hinge 606 connects the bottom half 602 and the top half 604 such that the top half 604 may move up and down in direction A in relation to the bottom half 602. In operation, a user places a breakable capsule 104 in the space 608 formed between the top half 604 and the bottom half 602 such that the capsule 104 is positioned near the hinge 606. The bottom half 602 may optionally have a shallow recessed portion 610, or a groove, in its surface which has a shape that is adapted for receiving the capsule 104. The user then applies a downward pressure on the top half 604 resulting in breaking the capsule 104 within the capsule breaking mechanism 600. The shallow recessed portion 610 assists in holding the capsule 104 within the capsule breaking mechanism 600 during use, thereby preventing the capsule 104 from sliding out of the capsule breaking mechanism 600.

The capsule breaking mechanism 600 is sized according to the housing 102, 202, 302, and 500 being used. That is, the capsule breaking mechanism 600 is sized to fit within the selected housing 102, 202, 302, and 500 such that the user may simply snap the top half 604 and bottom half 602 of the capsule breaking mechanism 600 together to break the capsule 104. The use of a capsule breaking mechanism 600 facilitates the use of the present invention and eliminates the possibility of the user getting cyanoacrylate monomer 108 on his/her fingers and hands, or feet if stepping on the top half 604, when breaking the capsule 104. In addition, the width of the capsule breaking mechanism 600 is preferably narrower than the length of the capsule 104. Thus when the capsule 104 is broken within the housing 102, 202, 302, 500 the capsule breaking mechanism 600 will not interfere with the emission of the resulting vapors 106.

The capsule breaking mechanism 600 may either be a separate component when using an apparatus 100, 200, 300, 500 of the present invention or may be previously affixed to the breakable capsules 104. Also, the entire disposable apparatus 100, 200, 300, 500 may be placed within a capsule breaking mechanism 600. Therefore, as a separate component, a user may reuse the capsule breaking mechanism 600 for multiple uses by simply removing the broken capsule 104 and replacing it with a new capsule 104. Alternatively, a capsule breaking mechanism 600 may be shipped with a capsule 104 already disposed therein. The capsule 104 may be secured to the bottom half 602 of the capsule breaking mechanism 600 by a fastener or adhesive to prevent movement during shipping. In this embodiment, the capsule breaking mechanism 600 is a disposable component along with the capsule 104. In yet another embodiment, the capsule breaking mechanism 600 with a breakable capsule 104 enclosed within a housing 102, 202, 302, 500 forms an integrated package.

Figure 7:
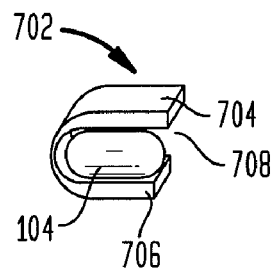
FIG. 7 is a perspective view of an alternative capsule mechanism.

FIG. 7 is a perspective view of an alternative capsule breaking mechanism 702. In this embodiment, the capsule breaking mechanism 702 is a C-shaped device having a first end 704 and a second end 706 which form a internal space 708. The capsule breaking mechanism 702 is preferably made of a strong but flexible plastic or metal which allows the capsule breaking mechanism 702 to bend yet hold its shape. In operation, a breakable capsule 104 is disposed within the space 708 between the first end 704 and second end 706, such that upon applying pressure to the first end 704 and/or the second end 706, the capsule 104 breaks. The capsule 104 is optionally secured within the space 708 by an adhesive or similar means. Further, the capsule 104 may be oriented in any direction within the space 708 such that the capsule 104 is completely enclosed within the space 708 or that one or more ends of the capsule 104 extend beyond the capsule breaking mechanism 702. Similar to the capsule breaking mechanism 600 described above, the capsule breaking mechanism 702 shown in FIG. 7 may be prepackaged within a housing 102, 202, 302, and 500 for easy use.

Figure 8:
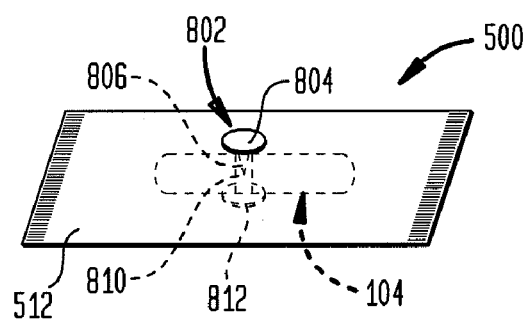
FIG. 8 is a perspective view of a second alternative capsule breaking mechanism.

FIG. 8 is a perspective view of a second alternative capsule breaking mechanism 802. In this embodiment, the capsule breaking mechanism 802 is a T-shaped device having a head 804 connected to a shaft 806 wherein the distal end of the shaft 806 is in communication with the surface of the breakable capsule 104 contained in a housing 512. The head 804 of the capsule breaking mechanism 802 may be located external to the housing 512 (as shown in FIG. 8) with the shaft 806 passing through the housing 512 surface to contact the capsule 104. In this embodiment, the distal end of the shaft 806 is held in place by the material of the housing 512. Alternatively, the entire capsule breaking mechanism 802 may be located within the housing 512 with the capsule 104. In this latter embodiment, the distal end of the shaft 806 is secured to the surface of the capsule 104 to ensure breakage.

In operation, a user presses the top of the head 804 of the capsule breaking mechanism 802 such that the distal end of the shaft 806, which may be sharp or have a point, to engage and break the capsule 104, thereby releasing the cyanoacrylate monomer 108 into the housing 512. The capsule 104 may have a groove 810 or similar dart, score, or etching on its exterior surface to facilitate the breaking of the capsule 104. Also, the capsule breaking mechanism 802 may include a bottom head 812 secured to and positioned on the side of the housing 512 opposite the head 804. In this embodiment, a user may place his/her fingers on both the head 804 and bottom head 812 and squeeze them together. The pressure from the squeezing will force the distal end of the shaft 806 to engage and break the capsule 104. Similar to the placement of the head 804, the bottom head 812 may be positioned within the housing 512 and secured to the side of the capsule 104 opposite the point at which the distal end of the shaft 806 is positioned.

Figure 9:
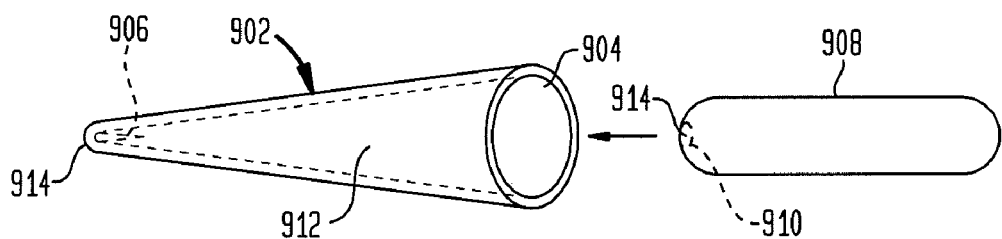
FIG. 9 is a perspective view of a third alternative capsule breaking mechanism.

FIG. 9 is a perspective view of a third alternative capsule breaking mechanism 906 which is incorporated into a housing 902. In this embodiment, the housing 902 is a tapered tube 912 having a closed end 914 and an open end 904, and contains a cyanoacrylate catalyst as described above. The capsule breaking mechanism 906 is a flange that extends from an interior surface of the closed end 914 into the internal chamber of the elongated tube 912 and terminates at a sharp or blunt distal end. A breakable capsule 908 containing the cyanoacrylate monomer 108 is inserted into the open end 904 of the housing 902 just before use. Upon insertion into the internal chamber of the housing 902, a first end 914 of the breakable capsule 908 engages the capsule breaking mechanism 906 which breaks the breakable capsule 908 and releases the cyanoacrylate monomer 108 into the internal chamber of the housing 102. As described above, the cyanoacrylate monomer 108 reacts with the cyanoacrylate catalyst contained in the housing 902 to create the vapor 106 for developing latent fingerprints. Optionally, the first end 914 of the breakable capsule 908 has a recessed portion 910 to facilitate the engagement of the capsule breaking mechanism 906 and the breaking of the breakable capsule 908.

The present invention is described in terms of any cyanoacrylate catalyst, which includes without limitation sodium silicate, sodium hydroxide, and any other "superglue" activator that causes the rapid polymerization of cyanoacrylate monomer into cyanoacrylate microcrystalline vapor 106.

In addition to the above embodiments, the housing 102, 202, 302, 500, 902 as well as the layer 304, of the present invention may be impregnated (in its entirety or a portion thereof) with a sublimation dye 510 along with a cyanoacrylate catalyst.

In yet another embodiment, the heat for vaporizing the cyanoacrylate monomer 108, or super glue, is provided by a separate chemical reaction in addition to or separate from the polymerization of the cyanoacrylate monomer 108 which is described above. In this embodiment, there is a breakable capsule 104 containing the cyanoacrylate monomer 108 and a second breakable capsule 504 containing a first chemical compound, both of which are placed within an internal chamber of a housing 102. The second breakable capsule 504 contains an cyanoacrylate accelerator which upon breaking the second breakable capsule 504, an exothermic reaction is initiated. The exothermic reaction results in the polymerization of the cyanoacrylate monomer 108 (when the first breakable capsule 104 is broken), which in turn produces the vapors 106 used to develop latent fingerprints.

In another related embodiment, the housing 102 contains a separate, second chemical compound. Similar to the cyanoacrylate catalyst described above, this separate second chemical compound is embedded within the fibers of the material of the housing 102 or is present in a separate layer 304, or liner, or otherwise disposed within the housing 102. The separate second chemical compound provides in some embodiments the primary source of heat for creating the vapor 106. In other embodiments, the heat of the separate second chemical compound provides additional heat for creating the vapors 106 in conjunction with the heat released by the polymerization of the cyanoacrylate monomer 108 and cyanoacrylate catalyst. The separate second chemical compound in one embodiment exothermically reacts in the presence of oxygen, such that when the housing 102 is removed from a protective wrapper, the separate second chemical compound begins to produce heat. In an alternative embodiment, the separate second chemical compound has an exothermic reaction with the cyanoacrylate monomer 108 (contained in the first breakable capsule 104) or with a first chemical compound contained in a second breakable capsule 504.

For example, a second breakable capsule 504 may contain water (the first chemical compound) while the separate second chemical compound contained in the housing 102 is anhydrous copper sulfate. Thus, upon breaking the first and second breakable capsules 104, 504, the first chemical compound (water) has an exothermic reaction with the second chemical compound (anhydrous copper sulfate) contained in the housing 102 which in turn polymerizes the cyanoacrylate monomer 108 from the first breakable capsule 104 and generates the vapor 106. The vapor 106 is then used to develop latent fingerprints as disclosed herein.

The apparatus of the present invention may be manufactured as self-contained packets available as single units or in multiple units such as blister packs. In this embodiment, the user simply has to open an outer wrapper, break the breakable capsule contained within the housing, and use as described for developing latent fingerprints. Alternatively, the housings, breakable capsules, and/or capsule breaking mechanisms may be packaged separately or in combination.

CONCLUSION

While various embodiments of the present invention have been described above, it should be understood that they have been presented by the way of example only, and not limitation. It will be understood by those skilled in the art that various changes in form and details may be made therein without departing from the spirit and scope of the invention as defined. Thus, the breadth and scope of the present invention should not be limited by any of the above-described exemplary embodiments.

What is claimed is:

1. An apparatus for developing latent fingerprints on objects, comprising:
   a breakable capsule containing a cyanoacrylate monomer; and
   a housing having an internal chamber and a means for emitting vapors, said housing containing a cyanoacrylate catalyst and said internal chamber adapted for receiving said breakable capsule.

2. The apparatus of claim 1, wherein said housing is made of a material impregnated with said cyanoacrylate catalyst.

3. The apparatus of claim 1, wherein said housing further comprising a layer containing said cyanoacrylate catalyst, said layer covering a portion of an interior surface of said housing.

4. The apparatus of claim 3, wherein said layer is selected from the group consisting of a direct application of said cyanoacrylate catalyst to said portion of said interior surface of said housing, and a liner within said internal chamber of said housing.

5. The apparatus of claim 1, wherein said breakable capsule is made of a material selected from the group consisting of thin glass, plastic, ceramic, composite, and resin coated paper.

6. The apparatus of claim 1, wherein said housing is made of a material selected from the group consisting of paper, fibrous textile, cellulosic fiber, plastic, resin, metal, and composite.

7. The apparatus of claim 1, wherein said means for emitting vapors are selected from the group consisting of said housing having perforations, pores, slots, one or more open ends, mesh, and porous material.

8. The apparatus of claim 1, further comprising a means for breaking said breaking capsule within said housing.

9. The apparatus of claim 8, wherein said means for breaking said capsule is a capsule breaking mechanism selected from the group consisting of: a mechanism having a top half and a bottom half pivotally connected, a C-shaped mechanism, a head with a shaft wherein a distal end of said shaft is adapted to engage an exterior surface of said capsule, and said housing incorporating a flange extending into said internal cavity.

10. The apparatus of claim 9, wherein said means for breaking said capsule is contained within said housing.

11. The apparatus of claim 1, wherein said housing further comprises a resealable side and a means for opening and closing said resealable side.

12. The apparatus of claim 1, further comprising a second breakable capsule containing a second catalyst.

13. The apparatus of claim 12, wherein said second catalyst is a sublimation dye.

14. The apparatus of claim 1, wherein said housing further comprises a sublimation dye.

15. The apparatus of claim 1, further comprising a sealed wrapper containing said housing and said breakable capsule.

16. The apparatus of claim 1, wherein said breakable capsule incorporates a means for facilitating breaking on a portion of its exterior surface, said means for facilitating breaking being selected from the group consisting of: a groove, an etching, a score, and a dart.

* * * * *

UNITED STATES PATENT AND TRADEMARK OFFICE
CERTIFICATE OF CORRECTION

PATENT NO. : 7,182,817 B1  Page 1 of 1
APPLICATION NO. : 11/406096
DATED : February 27, 2007
INVENTOR(S) : David E. Weaver et al.

It is certified that error appears in the above-identified patent and that said Letters Patent is hereby corrected as shown below:

Title Page, Insert: (60) U.S. Application Data claim to benefit of United States provisional application 60/672,285 filed April 18, 2005.

Signed and Sealed this

Thirteenth Day of May, 2008

JON W. DUDAS
*Director of the United States Patent and Trademark Office*